United States Patent
Bae et al.

(10) Patent No.: US 11,944,460 B2
(45) Date of Patent: Apr. 2, 2024

(54) METHOD AND APPARATUS FOR DETERMINING SHARPNESS OF PULSE WAVE SIGNAL

(71) Applicant: Korea Institute of Oriental Medicine, Daejeon (KR)

(72) Inventors: Jang Han Bae, Daejeon (KR); Young Ju Jeon, Daejeon (KR); Jong Yeol Kim, Daejeon (KR)

(73) Assignee: Korea Institute of Oriental Medicine, Daejeon (KR)

(*) Notice: Subject to any disclaimer, the term of this patent is extended or adjusted under 35 U.S.C. 154(b) by 1021 days.

(21) Appl. No.: 16/757,101

(22) PCT Filed: Sep. 18, 2018

(86) PCT No.: PCT/KR2018/010963
§ 371 (c)(1),
(2) Date: Apr. 17, 2020

(87) PCT Pub. No.: WO2019/078493
PCT Pub. Date: Apr. 25, 2019

(65) Prior Publication Data
US 2020/0245948 A1    Aug. 6, 2020

(30) Foreign Application Priority Data
Oct. 20, 2017   (KR) .................. 10-2017-0136227

(51) Int. Cl.
*A61B 5/00* (2006.01)
*A61B 5/02* (2006.01)
*A61B 5/024* (2006.01)

(52) U.S. Cl.
CPC ........ *A61B 5/7221* (2013.01); *A61B 5/02028* (2013.01); *A61B 5/024* (2013.01); *A61B 5/4854* (2013.01); *A61B 5/7235* (2013.01)

(58) Field of Classification Search
CPC ....... A61B 5/7264; A61B 5/318; A61B 5/316; A61B 5/02405; A61B 5/349; A61B 5/35;
(Continued)

(56) References Cited

U.S. PATENT DOCUMENTS

2010/0262022 A1* 10/2010 Baruch .................. A61B 5/021
600/500

FOREIGN PATENT DOCUMENTS

| JP | H08154906 A | 6/1996 |
| JP | 2002320594 A | 11/2002 |

(Continued)

OTHER PUBLICATIONS

Y. Christopher Chiu, MD, Patricia W. Arand, PhD, Sanjeev G. Shroff, PhD, Ted Feldman, MD, and John D. Carroll, MD, Chicago, Ill., Determination of pulse wave velocities with computerized algorithms, American Heart Journal, vol. 121, p. 1460-1470, 11 pages.

*Primary Examiner* — Paula J Stice
*Assistant Examiner* — Anh-Khoa N Dinh
(74) *Attorney, Agent, or Firm* — DALY, CROWLEY, MOFFORD & DURKEE, LLP

(57) ABSTRACT

A method for determining a sharpness index of a pulse wave signal includes receiving a pulse wave signal; determining a first reference line starting point and a second reference line starting point on the basis of a curvature of the pulse wave signal; determining a first reference line connecting the first reference line starting point and a first reference line ending point by determining the first reference line ending point by applying an intersecting tangent method to the first reference line starting point, and determining a second reference line connecting the second reference line starting point and a second reference line ending point by determining the second reference line ending point by applying the inter-
(Continued)

secting tangent method to the second reference line starting point; and determining a sharpness index by using a peak point of the pulse wave signal, the first reference line, and the second reference line.

17 Claims, 4 Drawing Sheets

(58) Field of Classification Search
CPC .............. A61B 18/12; A61B 18/14; A61B 2018/00351; A61B 2018/00595; A61B 2018/1467; A61B 5/021; A61B 5/0245; A61B 5/165; A61B 5/287; A61B 5/339; A61B 5/361; A61B 5/378; A61B 5/6852; A61B 5/02125; A61B 5/02042; A61B 5/7239; A61B 5/7275; A61B 2560/0223; A61B 2562/0247; A61B 5/02108; A61B 5/02116; A61B 5/0215; A61B 5/022; A61B 5/02225; A61B 5/026; A61B 5/7221; G16H 20/40; G16H 40/63; G16H 50/20; G16H 50/30; G16H 50/50; Y02A 90/10

See application file for complete search history.

(56) References Cited

FOREIGN PATENT DOCUMENTS

| | | |
|---|---|---|
| JP | 2004041244 A | 2/2004 |
| JP | 2007181628 | 7/2007 |
| KR | 1020020073374 A | 9/2002 |
| KR | 20100130108 A | 12/2010 |
| KR | 20110032107 A | 3/2011 |

\* cited by examiner

METHOD AND APPARATUS FOR DETERMINING SHARPNESS OF PULSE WAVE SIGNAL

CROSS REFERENCE TO RELATED APPLICATION

This application is a U.S. national stage filing under 35 U.S.C § 371 of PCT application number PCT/KR2018/010963 filed on Sep. 18, 2018, and entitled "METHOD AND APPARATUS FOR DETERMINING SHARPNESS OF PULSE WAVE SIGNAL," which is based on and claims the benefit of priority to Korean Patent Application No. 10-2017-0136227, filed Oct. 20, 2017 which applications are each hereby incorporated herein by reference in their entireties.

TECHNICAL FIELD

Embodiments relate to a method and apparatus for determining a sharpness of a pulse wave signal and, more particularly, to a method and apparatus for determining both reference lines near a peak point of a pulse wave signal through an intersecting tangent method and determining a sharpness index based on the reference lines.

BACKGROUND ART

One of the existing methods for determining a sharpness of a pulse wave signal is a method of finding both ending points of a width of a percussive wave based on ⅔ points of a peak point of a pulse wave signal and determining a sharpness based on a distance between both feature points and an angle formed by the ending points and the peak point of the pulse wave signal.

However, if the existing method is used, it was difficult to derive an accurate result with respect to a waveform where a tidal wave is generated at a higher position than the ⅔ points of the percussive wave.

That is, the existing method is applicable only to pulse wave signals of a specific type and thus, may not be uniformly applied to various types of pulse wave signals.

DISCLOSURE OF INVENTION

Technical Solutions

According to an aspect, there is provided a method of determining a sharpness index of a pulse wave signal, the method including receiving a pulse wave signal, determining a first reference line starting point and a second reference line starting point based on a curvature of the pulse wave signal, determining a first reference line connecting the first reference line starting point and a first reference line ending point by determining the first reference line ending point by applying an intersecting tangent method to the first reference line starting point, and determining a second reference line connecting the second reference line starting point and a second reference line ending point by determining the second reference line ending point by applying the intersecting tangent method to the second reference line starting point; and determining a sharpness index using a peak point of the pulse wave signal, the first reference line, and the second reference line.

The determining of the sharpness index may include determining an angle formed by a first feature point associated with the first reference line and a second feature point associated with the second reference line about the peak point of the pulse wave signal, and calculating the sharpness index based on the angle.

The determining of the angle may include determining, to be the first feature point, a point on the pulse wave signal corresponding to a point in time of an intersecting point of the first reference line and a horizontal straight line passing through the peak point of the pulse wave signal, and determining, to be the second feature point, a point on the pulse wave signal corresponding to a point in time of an intersecting point of the second reference line and the horizontal straight line passing through the peak point of the pulse wave signal.

The determining of the sharpness index may further include determining a height ratio of the height of the intersecting point of the first reference line and the second reference line to the height of the peak point of the pulse wave signal.

The calculating of the sharpness may include calculating the sharpness index based on the height ratio.

The calculating of the sharpness may include calculating the sharpness index by applying a first weight to the angle and applying a second weight to the height ratio.

The first reference line ending point may be determined to be an ending point closer to the peak point of the pulse wave signal than the first reference line starting point, among ending points detected by applying the intersecting tangent method to the first reference line starting point, and the second reference line ending point may be determined to be an ending point closer to the peak point of the pulse wave signal than the second reference line starting point, among ending points detected by applying the intersecting tangent method to the second reference line starting point.

The first reference line starting point may be determined to be a point at which a first derivative result of the pulse wave signal is maximized.

The second reference line starting point may be determined to be a point at which a second derivative result of the pulse wave signal is "0".

According to another aspect, there is provided an apparatus for determining a sharpness index of a pulse wave signal, the apparatus including a pulse wave signal receiver configured to receive a pulse wave signal, and a sharpness index determiner configured to determine a first reference line starting point and a second reference line starting point based on a curvature of the pulse wave signal, determine a first reference line connecting the first reference line starting point and a first reference line ending point by determining the first reference line ending point by applying an intersecting tangent method to the first reference line starting point, determine a second reference line connecting the second reference line starting point and a second reference line ending point by determining the second reference line ending point by applying the intersecting tangent method to the second reference line starting point, and determine a sharpness index using a peak point of the pulse wave signal, the first reference line, and the second reference line.

The sharpness index determiner may be configured to determine an angle formed by a first feature point associated with the first reference line and a second feature point associated with the second reference line about the peak point of the pulse wave signal, and calculate the sharpness index based on the angle.

The sharpness index determiner is configured to determine, to be the first feature point, a point on the pulse wave signal corresponding to a point in time of an intersecting point of the first reference line and a horizontal straight line passing through the peak point of the pulse wave signal, and determine, to be the second feature point, a point on the pulse wave signal corresponding to a point in time of an intersecting point of the second reference line and the horizontal straight line passing through the peak point of the pulse wave signal.

The sharpness index determiner may be configured to determine a height ratio of the height of the intersecting point of the first reference line and the second reference line to the height of the peak point of the pulse wave signal.

The sharpness index determiner may be configured to calculate the sharpness index based on the height ratio.

The sharpness index determiner may be configured to calculate the sharpness index by applying a first weight to the angle and applying a second weight to the height ratio.

The first reference line ending point may be determined to be an ending point closer to the peak point of the pulse wave signal than the first reference line starting point, among ending points detected by applying the intersecting tangent method to the first reference line starting point, and the second reference line ending point may be determined to be an ending point closer to the peak point of the pulse wave signal than the second reference line starting point, among ending points detected by applying the intersecting tangent method to the second reference line starting point.

The first reference line starting point may be determined to be a point at which a first derivative result of the pulse wave signal is maximized.

The second reference line starting point may be determined to be a point at which a second derivative result of the pulse wave signal is "0".

BEST MODE FOR CARRYING OUT THE INVENTION

Figure 1:
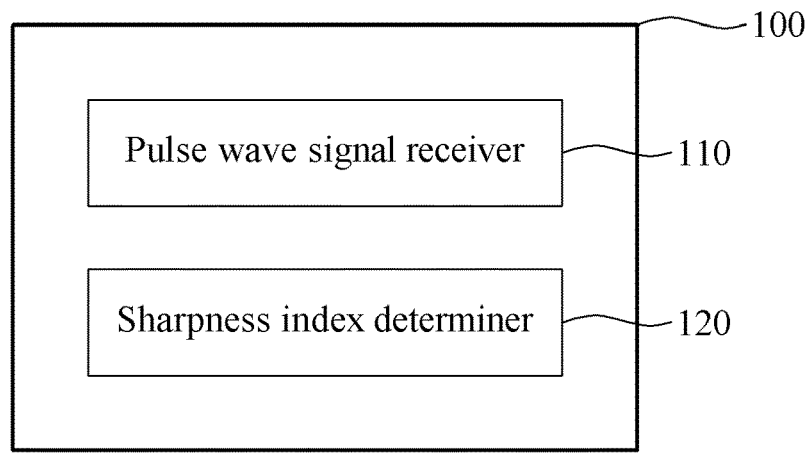
FIG. 1 is a block diagram schematically illustrating an apparatus for determining a sharpness of a pulse wave signal according to an embodiment.

Hereinafter, embodiments will be described in detail with reference to the accompanying drawings. The scope of the right, however, should not be construed as limited to the embodiments set forth herein. Like reference numerals in the drawings refer to like elements. The terms used herein are selected from terms generally understood by those skilled in the related art, but may have different meanings according to technical developments and/or changes, practices, and preferences of an engineer. Accordingly, the terms used herein should not be construed as limiting the technical spirit, and should be construed as illustrative terms to describe embodiments.

In addition, in a specific case, most appropriate terms are arbitrarily selected by the applicant. In this instance, the meanings of the arbitrarily used terms will be clearly explained in the corresponding description. Hence, the terms should be understood not by the simple names of the terms but by the meanings of the terms and the following overall description of this specification.

FIG. 1 is a block diagram schematically illustrating an apparatus 100 for determining a sharpness of a pulse wave signal according to an embodiment. The apparatus 100 for determining a sharpness of a pulse wave signal may include a pulse wave signal receiver 110 and a sharpness index determiner 120. Optionally, the apparatus 100 for determining a sharpness of a pulse wave signal may further include a communicator (not shown) configured to transmit information associated with a sharpness index and/or a display (not shown) configured to display the information associated with the sharpness index.

When the proposed apparatus 100 for determining a sharpness of a pulse wave signal is used, it is possible to supplement the disadvantage of the existing method that uniformly finds feature points based on ⅔ points of a peak point of a pulse wave signal.

In particular, to resolve the issue of deriving an inaccurate result depending on a type of a pulse wave signal, a method that obtains both reference lines of the pulse wave signal by applying an intersecting tangent method when determining feature points around a peak point of the pulse wave signal, determines feature points based on the reference lines, and determines a sharpness index through an angle with the peak point of the pulse wave signal is used. The sharpness index is an index defined to objectively indicate a sharpness characteristic of a pulse wave signal, and may represent a very accurate result even with respect to an irregular pulse wave signal or an unusual pulse wave signal.

Further, to additionally supplement the scheme of measuring a sharpness index based on such an angle, the height of an intersecting point of both reference lines may be quantified and reflected in the sharpness index.

In this way, the proposed apparatus 100 for determining a sharpness of a pulse wave signal may determine a sharpness index that uniformly quantifies features of various types of pulse wave signals. Further, the determined sharpness index may be effectively utilized to identify a pulse type such as a slippery pulse or a rough pulse in traditional Chinese medicine or Korean medicine.

The pulse wave signal receiver 110 may receive a pulse wave signal measured from a subject of measurement. For example, the pulse wave signal receiver 110 may receive the pulse wave signal in an analog or digital manner, and include a communicator including a wired or wireless communication device. The received pulse wave signal may include a signal measured in real time from the subject of measurement or a pulse wave signal measured and then stored in a recording medium.

The sharpness index determiner 120 may be implemented by a combination of hardware and/or software, and include predetermined appropriate elements to analyze and process the received pulse wave signal. Preferably, the sharpness index determiner 120 includes one or more processors and a memory.

The sharpness index determiner 120 may determine a first reference line starting point and a second reference line starting point based on a curvature of the pulse wave signal.

For example, the sharpness index determiner 120 may determine a point at which a first derivative result of the pulse wave signal is maximized to be the first reference line starting point, and determine a point at which a second derivative result of the pulse wave signal is "0" to be the second reference line starting point.

When the first reference line starting point and the second reference line starting point are determined, the sharpness index determiner 120 may determine a first reference line ending point by applying an intersecting tangent method to the first reference line starting point, and similarly, determine a second reference line ending point by applying the intersecting tangent method to the second reference line starting point. The intersecting tangent method have known as best performance algorithm for determining a starting point of a pulse wave, the details of which are described in the prior art document "Determination of pulse wave velocities with computerized algorithms".

When the intersecting tangent method is applied to a reference line starting point, it is possible to determine a point not satisfying constraints to be a reference line ending point by moving to the point not satisfying the constraints along a pulse wave signal line while the constraints are satisfied. In this example, a reference line ending point detected in a direction of a peak point of the pulse wave signal from the reference line start point, that is, an ending point closer to the peak point of the pulse wave signal than the reference line starting point, may be reflected in the determination of the sharpness index.

For example, the first reference line ending point may be determined to be an ending point closer to the peak point of the pulse wave signal than the first reference line starting point, among ending points detected by applying the intersecting tangent method to the first reference line starting point, and the second reference line ending point may be determined to be an ending point closer to the peak point of the pulse wave signal than the second reference line starting point, among ending points detected by applying the intersecting tangent method to the second reference line starting point.

In this way, when the first reference line starting point and the first reference line ending point are determined, a straight line connecting the first reference line starting point and the first reference line ending point may be determined to be a first reference line, and similarly, when the second reference line starting point and the second reference line ending point are determined, a straight line connecting the second reference line starting point and the second reference line ending point may be determined to be a second reference line.

When the first reference line and the second reference line are determined, the sharpness index determiner 120 may determine, to be a first feature point, a point on the pulse wave signal corresponding to a point in time of an intersecting point of the first reference line and a horizontal straight line passing through the peak point of the pulse wave signal, and determine, to be a second feature point, a point on the pulse wave signal corresponding to a point in time of an intersecting point of the second reference line and the horizontal straight line passing through the peak point of the pulse wave signal.

When the first feature point and the second feature point are determined, the sharpness index determiner 120 may determine an angle formed by the first feature point and the second feature point about the peak point of the pulse wave signal, and calculate a sharpness index based on the angle. The sharpness index may be expressed in a predetermined form capable of indicating a value or a level. For example, a relatively great angle may represent a relatively low sharpness.

The sharpness index determiner 120 may determine a height ratio of the height of the intersecting point of the first reference line and the second reference line to the height of the peak point of the pulse wave signal, and reflect the height ratio in the determination of the sharpness index. For example, the sharpness index determiner 120 may determine the sharpness index based on the height ratio of the height of the intersecting point of the first reference line and the second reference line to the height of the peak point of the pulse wave signal, together with the angle or instead of the angle.

The sharpness index determiner 120 may calculate the sharpness index through a multiplying operation of the angle and the height ratio. In another example, the sharpness index determiner 120 may calculate the sharpness index by applying a first weight to the angle, applying a second weight to the height ratio, and adding up the weighted angle and the weighted height ratio. Here, the first weight and the second weight may be predetermined to be values that may most effectively reflect the features of the pulse wave signal in the sharpness index.

There are various types of pulse wave signals of a subject of measurement in practice. However, the existing scheme calculates a sharpness simply based on ⅔ points of a peak point of a pulse wave signal in many cases. On the contrary, the proposed sharpness index may relatively flexibly handle various types and anomalous forms of pulse wave signals and reflect more accurate results. The proposed method of determining a sharpness will be described further with reference to exemplary pulse wave signals.

Figure 2:
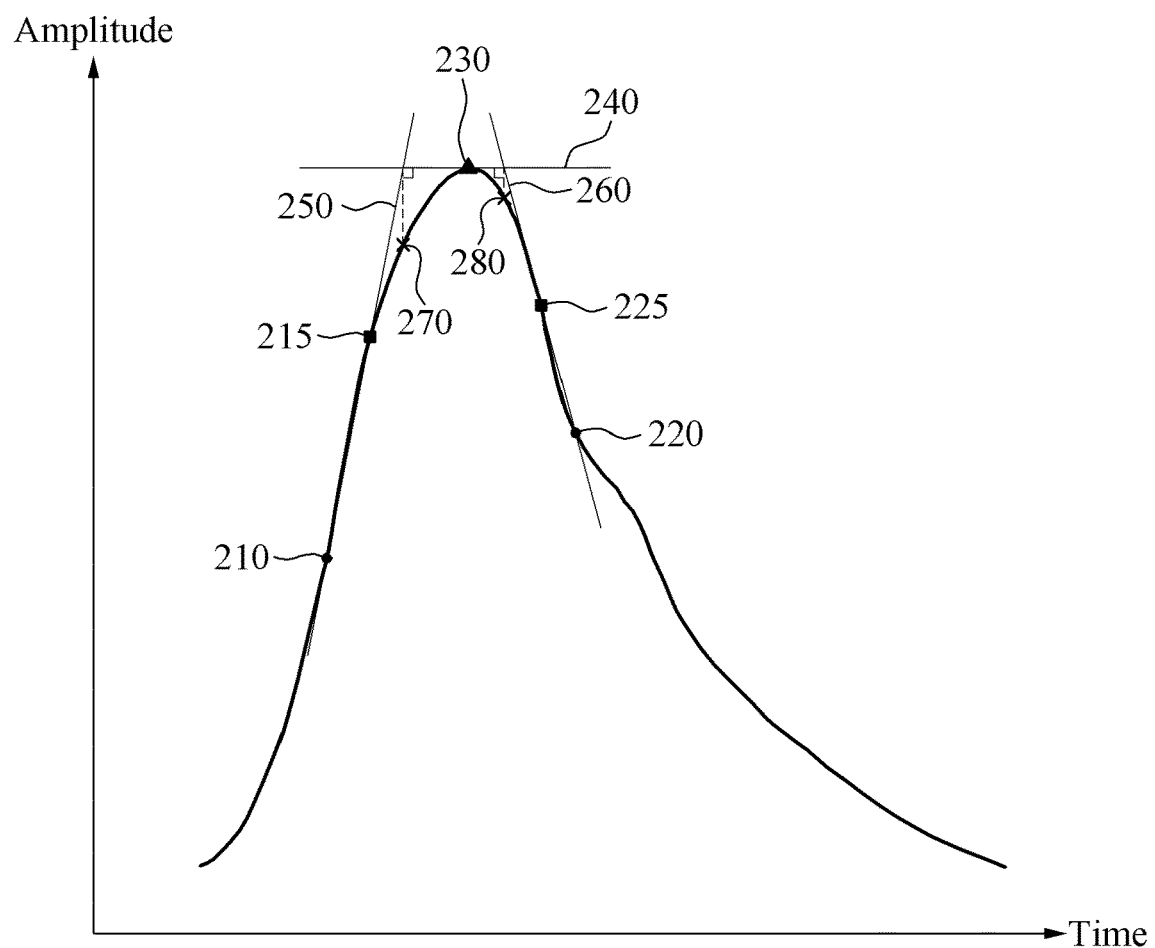
FIG. 2 is a graph to describe a method of determining a sharpness of a pulse wave signal according to an embodiment.

FIG. 2 is a graph to describe a method of determining a sharpness of a pulse wave signal according to an embodiment. In FIG. 2, an example of a type of a pulse wave signal is illustrated for description. Hereinafter, a process of determining a first feature point 270 and a second feature point 280 will be described with reference to FIG. 2.

A point at which a first derivative result of the pulse wave signal is maximized may be determined to be a first reference line starting point 210 through a mathematical operation, and a point at which a second derivative result of the pulse wave signal is "0" may be determined to be a second reference line starting point 220 through a mathematical operation.

When the first reference line starting point 210 and the second reference line starting point 220 are determined, a first reference line ending point 215 and a second reference line ending point 225 may be determined respectively by applying an intersecting tangent method to the first reference line starting point 210 and the second reference line starting point 220 in a direction of a peak point 230 of the pulse wave signal, in the manner described with reference to FIG. 1.

When the first reference line starting point 210 and the first reference line ending point 215 are determined, a straight line connecting the first reference line starting point and the first reference line ending point may be determined to be a first reference line 250, and similarly, when the second reference line starting point 220 and the second reference line ending point 225 are determined, a straight line connecting the second reference line starting point and the second reference line ending point may be determined to be a second reference line 260.

When the first reference line 250 and the second reference line 260 are determined, a point on the pulse wave signal corresponding to a point in time (that is, an x-coordinate on the graph) of an intersecting point of the first reference line 250 and a horizontal straight line 240 passing through the peak point 230 of the pulse wave signal may be determined to be the first feature point 270, and a point on the pulse wave signal corresponding to a point in time of an intersecting point of the second reference line 260 and the horizontal straight line 240 passing through the peak point 230 of the pulse wave signal may be determined to be the second feature point 280.

Figure 3:
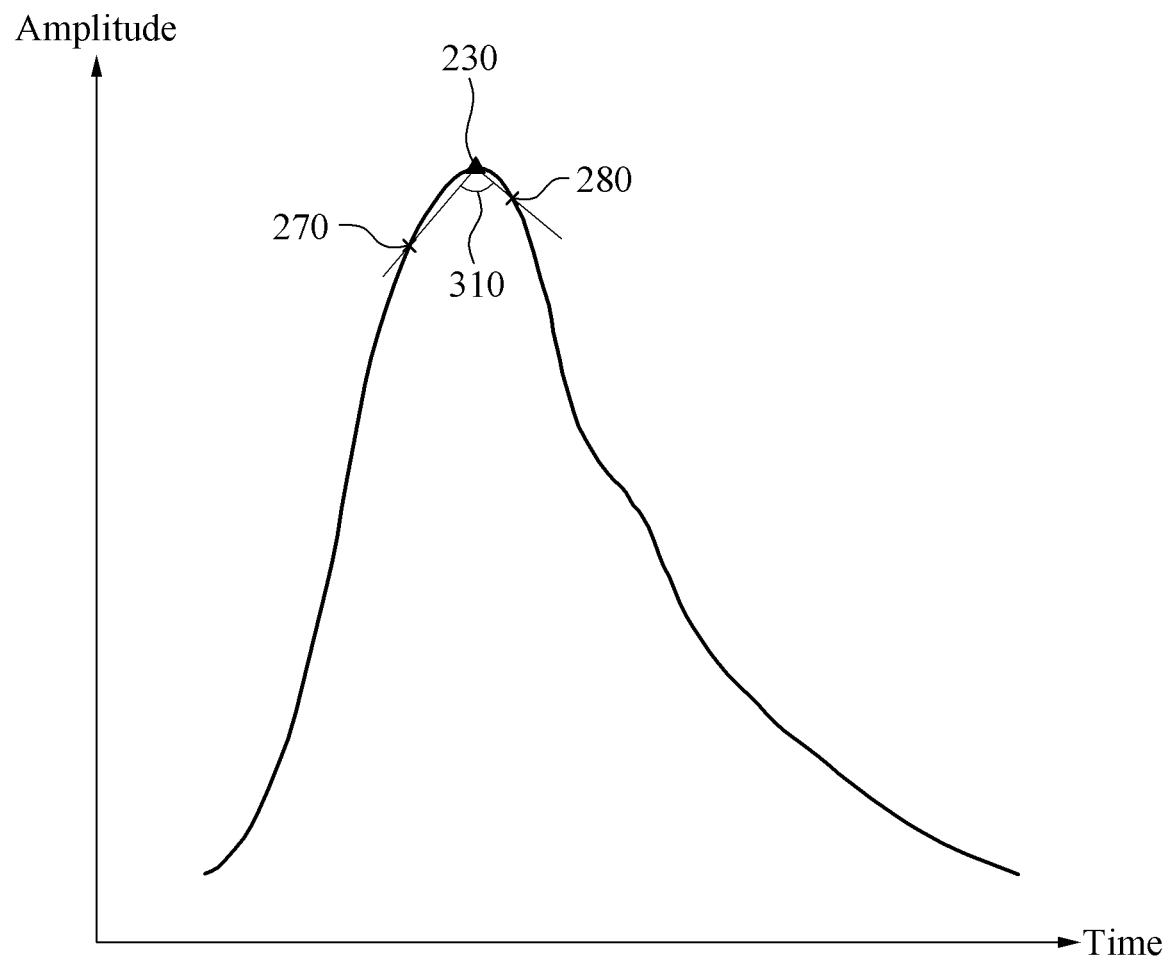
FIG. 3 is a graph to describe a method of determining a sharpness of a pulse wave signal according to an embodiment.

FIG. 3 is a graph to describe a method of determining a sharpness of a pulse wave signal according to an embodiment. In FIG. 3, an example of a type of a pulse wave signal is illustrated for description.

When the first feature point 270 and the second feature point 280 on the left and right of the peak point 230 of the pulse wave signal are determined in the manner described with reference to FIG. 2, an angle 310 formed by the first feature point 270 and the second feature point 280 about the peak point 230 of the pulse wave signal may be determined as a parameter to be reflected in the determination of a sharpness index, and the sharpness index may be calculated based on the angle 310.

As shown in the graph, the sharpness may decrease as the angle 310 increases, and the sharpness may increase as the angle 310 decreases.

Figure 4:
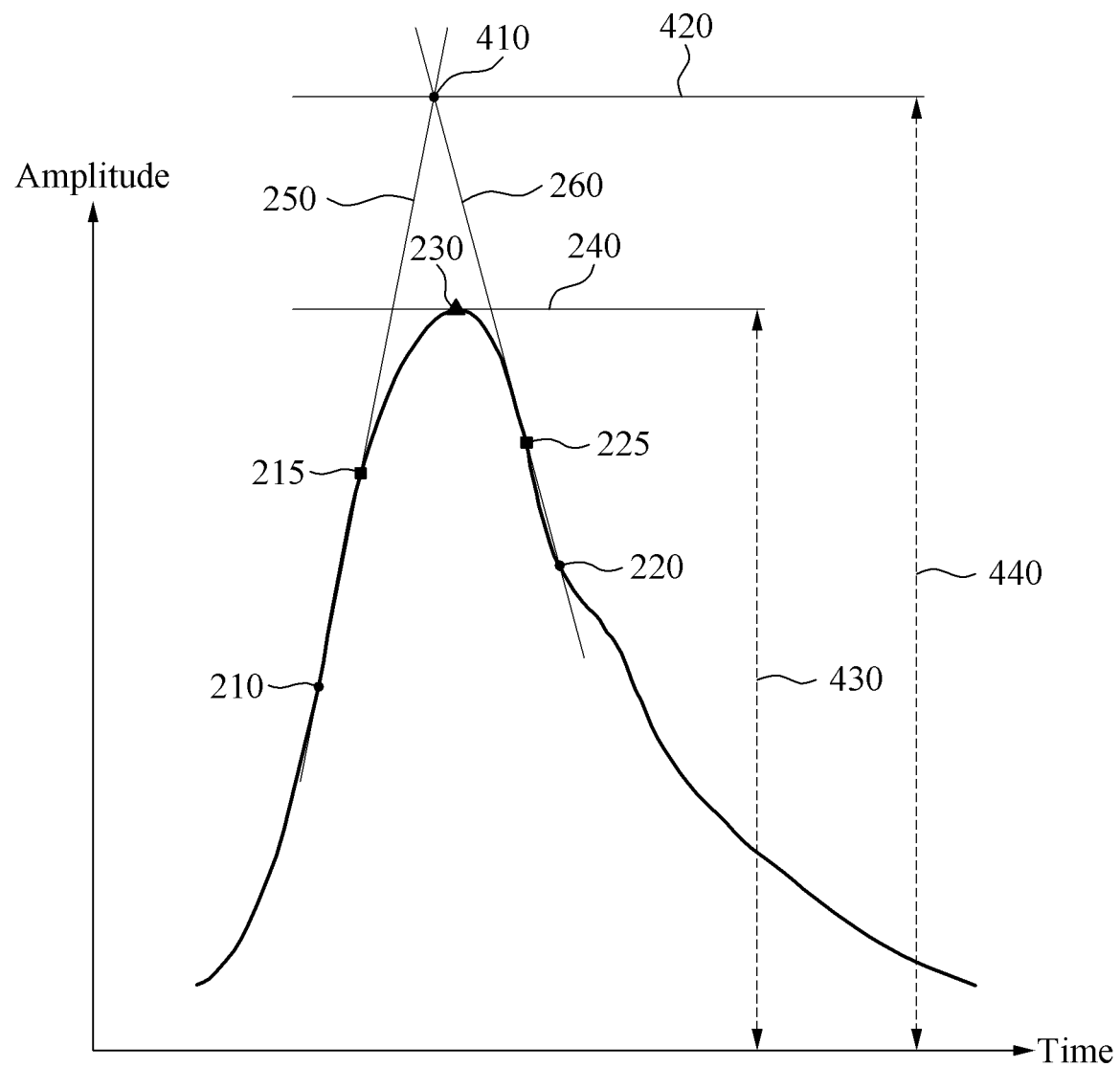
FIG. 4 is a graph to describe a method of determining a sharpness of a pulse wave signal according to an embodiment.

FIG. 4 is a graph to describe a method of determining a sharpness of a pulse wave signal according to an embodiment. In FIG. 4, an example of a type of a pulse wave signal is illustrated for description.

When the first reference line 250 and the second reference line 260 on the left and right of the peak point 230 of the pulse wave signal are determined in the manner described with reference to FIG. 2, the height 440 of an intersecting point 410 of the first reference line 250 and the second reference line 260 may be calculated. The height 440 of the intersecting point 410 of the first reference line 250 and the second reference line 260 has a value that varies depending on the shape of a pulse wave and thus, may be reflected in the determination of the sharpness index.

For example, a height ratio of the height 440 of the intersecting point 410 of the first reference line 250 and the second reference line 260 to the height 430 of the peak point 230 of the pulse wave signal may be determined, and the height ratio may be reflected in the determination of the sharpness index.

Figure 5:
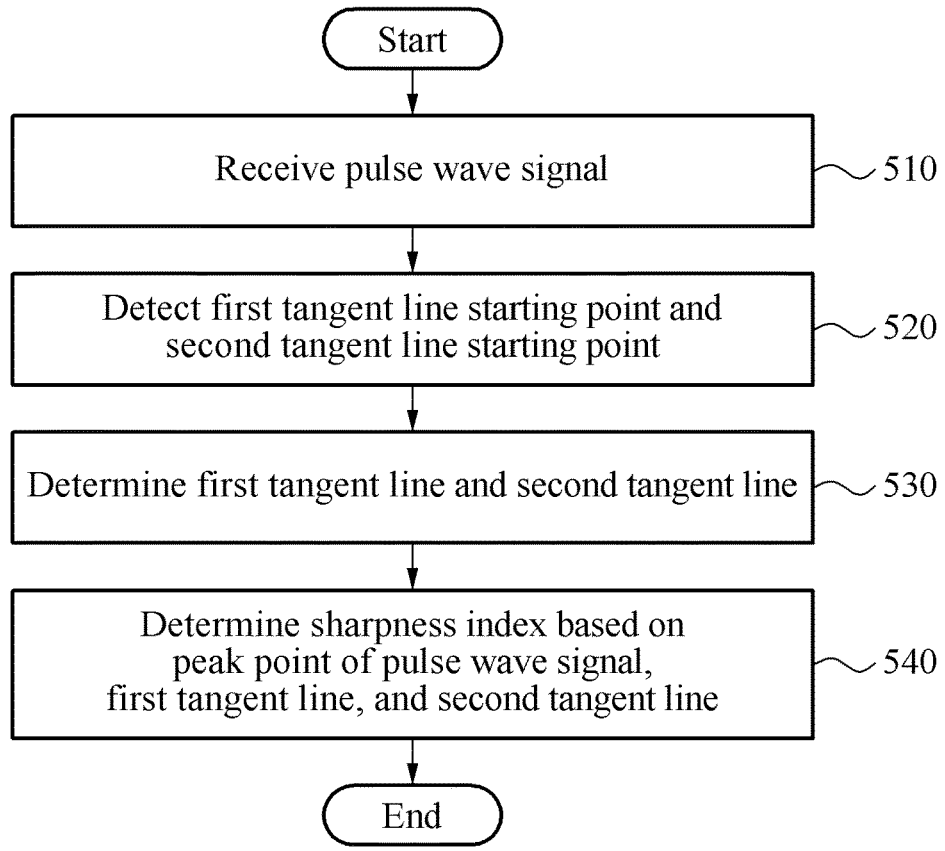
FIG. 5 is a flowchart to describe a method of determining a sharpness of a pulse wave signal according to an embodiment.

FIG. 5 is a flowchart to describe a method of determining a sharpness of a pulse wave signal according to an embodiment. The method of determining a sharpness shown in FIG. 5 may be performed, for example, by the apparatus for determining a sharpness of FIG. 1.

In operation 510, a pulse wave signal measured from a subject of measurement may be received. For example, the pulse wave signal may be received in an analog or digital manner, and may be received using a wired or wireless communication device. The received pulse wave signal may include a signal measured in real time from the subject of measurement or a pulse wave signal measured and then stored in a recording medium.

In operation 520, a first reference line starting point and a second reference line starting point may be determined based on the pulse wave signal. In detail, a point at which a first derivative result of the pulse wave signal is maximized may be determined to be the first reference line starting point, and a point at which a second derivative result of the pulse wave signal is "0" may be determined to be the second reference line starting point.

In operation 530, a first reference line and a second reference line may be determined. In detail, a first reference line ending point may be determined by applying an intersecting tangent method to the first reference line starting point, and similarly, a second reference line ending point may be determined by applying the intersecting tangent method to the second reference line starting point. When the first reference line starting point and the first reference line ending point are determined, a straight line connecting the first reference line starting point and the first reference line ending point may be determined to be the first reference line, and similarly, when the second reference line starting point and the second reference line ending point are determined, a straight line connecting the second reference line starting point and the second reference line ending point may be determined to be the second reference line.

In operation 540, a sharpness index may be determined based on the peak point of the pulse wave signal, the first reference line, and the second reference line. The sharpness index is an index defined to objectively indicate a sharpness characteristic of a pulse wave signal, and the process of determining a sharpness index will be described further below with reference to FIG. 6.

Figure 6:
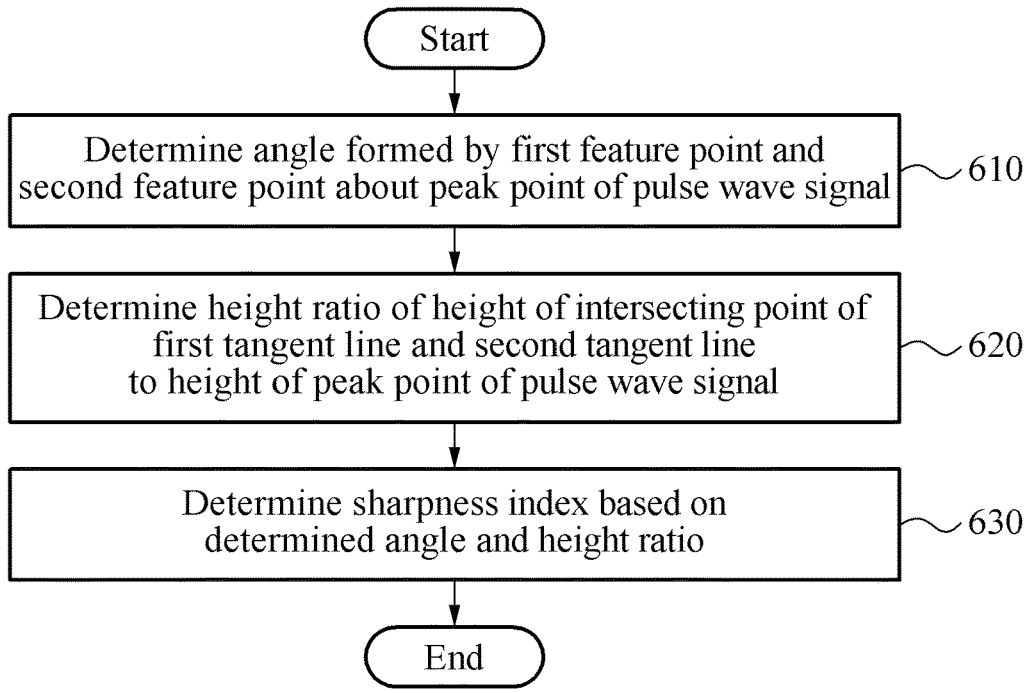
FIG. 6 is a flowchart to describe a method of determining a sharpness of a pulse wave signal according to an embodiment.

FIG. 6 is a flowchart to describe a method of determining a sharpness of a pulse wave signal according to an embodiment. The method of determining a sharpness shown in FIG. 6 may be performed, for example, by the apparatus for determining a sharpness of FIG. 1.

In operation 610, an angle formed by a first feature point associated with the first reference line and a second feature point associated with the second reference line about the peak point of the pulse wave signal may be determined. In detail, a point on the pulse wave signal corresponding to a point in time of an intersecting point of the first reference line and a horizontal straight line passing through the peak point of the pulse wave signal may be determined to be the first feature point, and a point on the pulse wave signal corresponding to a point in time of an intersecting point of the second reference line and the horizontal straight line passing through the peak point of the pulse wave signal may be determined to be the second feature point. When the first feature point and the second feature point are determined, the angle formed by the first feature point and the second feature point about the peak point of the pulse wave signal may be determined.

In operation 620, a height ratio of the height of the intersecting point of the first reference line and the second reference line to the height of the peak point of the pulse wave signal may be determined. The height of the intersecting point of the first reference line and the second reference line has a value that varies depending on the shape of a pulse wave and thus, may be reflected in the determination of the sharpness index.

In operation 630, a sharpness index may be calculated based on the angle determined in operation 610 and the height ratio determined in operation 620. For example, the sharpness index may be calculated through a multiplying operation of the angle and the height ratio. Alternatively, the sharpness index may be calculated by applying a first weight to the angle, applying a second weight to the height ratio, and adding up the weighted angle and the weighted height ratio. Here, the first weight and the second weight may be predetermined to be values that may most effectively reflect the features of the pulse wave signal in the sharpness index.

As described above, it is possible to represent a sharpness characteristic of a pulse wave using an objective and quantitative index by determining a sharpness index of a pulse wave signal in a manner that is uniformly applicable to various types of pulse wave signals.

Further, it is possible to infer a cardiovascular condition including arterial stiffness and to contribute to an objective diagnosis of a pulse type such as a slippery pulse or a rough pulse associated with a degree of sharpness of a pulse wave using a sharpness index.

The units described herein may be implemented using a hardware component, a software component and/or a combination thereof. A processing device may be implemented using one or more general-purpose or special-purpose computers, such as, for example, a processor, a controller and an arithmetic logic unit (ALU), a DSP, a microcomputer, an FPGA, a programmable logic unit (PLU), a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciate that a processing device may include multiple processing elements and multiple types of processing elements. For example, the processing device may include a plurality of processors, or a single processor and a single controller. In addition, different processing configurations are possible, such a parallel processors.

The software may include a computer program, a piece of code, an instruction, or some combination thereof, to independently or collectively instruct or configure the processing device to operate as desired. Software and data may be embodied permanently or temporarily in any type of machine, component, physical or virtual equipment, computer storage medium or device, or in a propagated signal wave capable of providing instructions or data to or being interpreted by the processing device. The software also may be distributed over network-coupled computer systems so that the software is stored and executed in a distributed fashion. The software and data may be stored by one or more non-transitory computer-readable recording mediums.

The methods according to the above-described examples may be recorded in non-transitory computer-readable media including program instructions to implement various operations of the above-described examples. The media may also include, alone or in combination with the program instructions, data files, data structures, and the like. The program instructions recorded on the media may be those specially designed and constructed for the purposes of examples, or they may be of the kind well-known and available to those having skill in the computer software arts. Examples of non-transitory computer-readable media include magnetic media such as hard disks, floppy disks, and magnetic tape; optical media such as CD-ROM discs. DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher-level code that may be executed by the computer using an interpreter. The above-described devices may be configured to act as one or more software modules in order to perform the operations of the above-described examples, or vice versa.

A number of exemplary embodiments have been described above. Nevertheless, it should be understood that various modifications may be made to these exemplary embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

The invention claimed is:

1. A method of determining a sharpness index of a pulse wave signal, the method comprising:
   receiving a pulse wave signal;
   determining a first reference line starting point and a second reference line starting point based on a curvature of the pulse wave signal, wherein the first reference line starting point is determined to be a point at which a first derivative result of the pulse wave signal is maximized;
   determining a first reference line connecting the first reference line starting point and a first reference line ending point by determining the first reference line ending point by applying an intersecting tangent method to the first reference line starting point, and determining a second reference line connecting the second reference line starting point and a second reference line ending point by determining the second reference line ending point by applying the intersecting tangent method to the second reference line starting point; and
   determining a sharpness index using a peak point of the pulse wave signal, the first reference line, and the second reference line.

2. The method of claim 1, wherein the determining of the sharpness index comprises:
   determining an angle formed by a first feature point associated with the first reference line and a second feature point associated with the second reference line about the peak point of the pulse wave signal; and
   calculating the sharpness index based on the angle.

3. The method of claim 2, wherein the determining of the angle comprises:
   determining, to be the first feature point, a point on the pulse wave signal corresponding to a point in time of an intersecting point of the first reference line and a horizontal straight line passing through the peak point of the pulse wave signal; and
   determining, to be the second feature point, a point on the pulse wave signal corresponding to a point in time of an intersecting point of the second reference line and the horizontal straight line passing through the peak point of the pulse wave signal.

4. The method of claim 2, wherein the determining of the sharpness index further comprises:
   determining a height ratio of the height of the intersecting point of the first reference line and the second reference line to the height of the peak point of the pulse wave signal.

5. The method of claim 4, wherein the calculating of the sharpness comprises calculating the sharpness index based on the height ratio.

6. The method of claim 5, wherein the calculating of the sharpness comprises calculating the sharpness index by applying a first weight to the angle and applying a second weight to the height ratio.

7. The method of claim 1, wherein the first reference line ending point is determined to be an ending point closer to the peak point of the pulse wave signal than the first reference line starting point, among ending points detected by applying the intersecting tangent method to the first reference line starting point, and the second reference line ending point is determined to be an ending point closer to the peak point of the pulse wave signal than the second reference line starting point, among ending points detected by applying the intersecting tangent method to the second reference line starting point.

8. The method of claim 1, wherein the second reference line starting point is determined to be a point at which a second derivative result of the pulse wave signal is "0".

9. A non-transitory computer-readable storage medium storing instructions that, when executed by a processor, cause the processor to perform the method of claim 1.

10. An apparatus for determining a sharpness index of a pulse wave signal, the apparatus comprising:

a pulse wave signal receiver configured to receive a pulse wave signal; and a sharpness index determiner configured to determine a first reference line starting point and a second reference line starting point based on a curvature of the pulse wave signal, determine a first reference line connecting the first reference line starting point and a first reference line ending point by determining the first reference line ending point by applying an intersecting tangent method to the first reference line starting point, wherein the first reference line starting point is determined to be a point at which a first derivative result of the pulse wave signal is maximized, determine a second reference line connecting the second reference line starting point and a second reference line ending point by determining the second reference line ending point by applying the intersecting tangent method to the second reference line starting point, and determine a sharpness index using a peak point of the pulse wave signal, the first reference line, and the second reference line.

11. The apparatus of claim 10, wherein the sharpness index determiner is configured to:

determine an angle formed by a first feature point associated with the first reference line and a second feature point associated with the second reference line about the peak point of the pulse wave signal, and calculate the sharpness index based on the angle.

12. The apparatus of claim 11, wherein the sharpness index determiner is configured to:

determine, to be the first feature point, a point on the pulse wave signal corresponding to a point in time of an intersecting point of the first reference line and a horizontal straight line passing through the peak point of the pulse wave signal, and determine, to be the second feature point, a point on the pulse wave signal corresponding to a point in time of an intersecting point of the second reference line and the horizontal straight line passing through the peak point of the pulse wave signal.

13. The apparatus of claim 11, wherein the sharpness index determiner is configured to:

determine a height ratio of the height of the intersecting point of the first reference line and the second reference line to the height of the peak point of the pulse wave signal.

14. The apparatus of claim 13, wherein the sharpness index determiner is configured to calculate the sharpness index based on the height ratio.

15. The apparatus of claim 14, wherein the sharpness index determiner is configured to calculate the sharpness index by applying a first weight to the angle and applying a second weight to the height ratio.

16. The apparatus of claim 10, wherein the first reference line ending point is determined to be an ending point closer to the peak point of the pulse wave signal than the first reference line starting point, among ending points detected by applying the intersecting tangent method to the first reference line starting point, and the second reference line ending point is determined to be an ending point closer to the peak point of the pulse wave signal than the second reference line starting point, among ending points detected by applying the intersecting tangent method to the second reference line starting point.

17. The apparatus of claim 10, wherein the second reference line starting point is determined to be a point at which a second derivative result of the pulse wave signal is "0".

* * * * *